(12) United States Patent
Lee

(10) Patent No.: US 9,889,125 B2
(45) Date of Patent: *Feb. 13, 2018

(54) METHODS FOR TREATING HEARTBURN, GASTRIC BLEEDING OR HEMORRHAGE IN PATIENTS RECEIVING CLOPIDOGREL THERAPY

(71) Applicant: TAKEDA PHARMACEUTICALS U.S.A., INC., Deerfield, IL (US)

(72) Inventor: Ronald D. Lee, Round Lake Beach, IL (US)

(73) Assignee: TAKEDA PHARMACEUTICALS U.S.A., INC., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/940,064

(22) Filed: Nov. 12, 2015

(65) Prior Publication Data

US 2016/0128995 A1 May 12, 2016

Related U.S. Application Data

(63) Continuation of application No. 13/411,701, filed on Mar. 5, 2012, now Pat. No. 9,233,103.

(60) Provisional application No. 61/467,545, filed on Mar. 25, 2011.

(51) Int. Cl.
| | |
|---|---|
| *A61K 31/535* | (2006.01) |
| *A61K 31/44* | (2006.01) |
| *A61K 31/4439* | (2006.01) |
| *A61K 31/4365* | (2006.01) |

(52) U.S. Cl.
CPC ...... *A61K 31/4439* (2013.01); *A61K 31/4365* (2013.01); *A61K 31/44* (2013.01)

(58) Field of Classification Search
CPC . A61K 31/4365; A61K 31/4439; A61K 31/44
USPC ..................... 514/233.8, 301, 338
See application file for complete search history.

(56) References Cited

U.S. PATENT DOCUMENTS

| | | | | |
|---|---|---|---|---|
| 8,173,158 B2 * | 5/2012 | Lee | ...... | A61K 9/5026 424/451 |
| 9,233,103 B2 * | 1/2016 | Lee | ...... | A61K 31/4365 |
| 2008/0166423 A1 | 7/2008 | Sundharadas | | |
| 2011/0212090 A1 | 9/2011 | Pedersen et al. | | |

FOREIGN PATENT DOCUMENTS

| | | |
|---|---|---|
| WO | 2005/026174 | 3/2005 |
| WO | 2009/105234 | 8/2009 |
| WO | 2010/047756 | 4/2010 |

OTHER PUBLICATIONS

Abel, C. et al., "Dexlansoprazole in the treatment of esophagitis and gastroesophageal reflux disease," Annals of Pharmacotherapy, Harvey Whitney Books Company (2010) 44(5):871-877.
Angiolilo et al., "Differential effects of omperazole and pantoprazole on the pharmacodynamics and pharmacokinetics of clopidrogrel in healthy subjects: randomized, placebo-controlled crossover comparison studies," Clinical Pharmacology & Therapeutics (2011) 89(1):65-74.
Anonymous, "New study results presented on Dexlansoprazole and Lansoprazole effects of Plavix (clopidogrel bisulfate)," Apr. 5, 2011, retrieved from the Internet: URL:http://www.tpna.com/newsroom/press_release_detail.aspx?, retrieved on May 14, 2012.
Anonymous, Dexilant (Dexlansoprazole) co-administration with Plavix (Clopidogrel bisulfate), product information updated, Nov. 18, 2011, retrieved from the Internet: URL:http://medicalnewstotay.com/articles/237939.php, retrieved on May 14, 2012.
Bruley Des Varannes, S. et al., Best Practice and Research Clinical Gastroenterology (2010) 24:905-921.
Cash, B.D. et al., "The role of PPIs/acid-suppresive agents in the management of GERD and related conditions," Advances in GERD/Acid-Related Disorders: Highlights from New Orleans 2010 (2010).
Croxtall, J.D. et al., Drugs (2010) 70(12):1593-1601.
Emerson, C.R. et al., Clinical Therapeutics (2010) 32(9):1578-1596.
Friedlander, E.A. et al., J. Amer. Acad. Nurse Practitioners (2010) 22(12):674-692.
Furuta, T. et al., "Influences of different proton pump inhibirots on the anti-platelet function of clopidogrel in relation to CYP2C19 genotypes," Br. J. Clin. Pharmacol. (2010) 70(3):383-392.
Gremmel, T., "The influence of proton pump inhibitors on the antiplatelet potency of clopidogrel evaluation by five different platelet function tests," J. Cardiovasc. Pharmacol. (2010) 56(5):532-539.
http://www.iffgd.org/site.news-events/news/industry-news/kapidex-dexilant.
International Search Report in corresponding PCT application PCT/US2012/029332 dated Jun. 11, 2012.
International Preliminary Report on Patentability for Application No. PCT/US2012/0293332 dated Oct. 10, 2013.
Johnson, D.A., Curr. Gastroenterol. Rep. (2010) 12:167-174.
Ly, V. et al., Expert Rev. Clin. Pharmacol. (2010) 3(1):89-102.
McConathy et al., "Stereochemistry in drug action," Prim. Care Companion J. Clin. Psychiatry (2003) 5(2):70-73.
Ogawa, R. et al., Clin. Pharmacokinet. (2010) 49(8):509-533.
Ogilvie, B.W. et al., "The proton pump inhibitor, omeprazole, but not lansoprazole or pantoprazole, is a metabolism-dependent inhibitor of CYP2C19: implications for coadministration with Clopidogrel," Drug Metabolism and Disposition (2011) 39(11):2020-2033.
Oyetayo, O.O. et al., Expert Opin. Drug Saf. (2010) 9(4):593-602.
Small, D.S. et al., J. Clin. Pharmacol. (2008) 48:475-484.
Tran, M. et al., J. Cardio. Pharmacol. Therap. (2010) 15(4):326-337.
Vakily, M. et al., Clin. Drug. Invest. (2009) 29(1):35-50.
Yang, J-C. et al., Expert Opin. Drug Metab. Toxicol. (2010) 6(1):29-41.

* cited by examiner

*Primary Examiner* — Kevin E Weddington
(74) *Attorney, Agent, or Firm* — Michael Best & Friedrich LLP

(57) ABSTRACT

The present invention relates to methods of treating heartburn in a patient receiving clopidogrel therapy. In another aspect, the present invention relates to methods of preventing gastric bleeding or hemorrhage in patients receiving clopidogrel therapy.

10 Claims, No Drawings

METHODS FOR TREATING HEARTBURN, GASTRIC BLEEDING OR HEMORRHAGE IN PATIENTS RECEIVING CLOPIDOGREL THERAPY

CROSS-REFERENCE TO RELATED APPLICATION(S)

This is a continuation of U.S. patent application Ser. No. 13/411,701, filed on Mar. 5, 2012, which claims priority to U.S. Provisional Patent Application No. 61/467,545, filed on Mar. 25, 2011, the entire contents of all of which are fully incorporated herein by reference.

FIELD OF THE INVENTION

The present invention relates to methods of treating heartburn in a patient receiving clopidogrel therapy. In another aspect, the present invention relates to methods of preventing gastric bleeding or hemorrhage in patients receiving clopidogrel therapy.

BACKGROUND

Clopidogrel bisulfate (currently sold under the brand name Plavix; clopidogrel bisulfate will occasionally be referred to herein simply as "clopidogrel") is a thienopyridine class inhibitor of $P2Y_{12}$ ADP platelet receptors. Chemically, it is referred to as methyl (+)-(S)-α-(2-chlorophenyl)-6,7-dihydrothieno[3,2-c]pyridine-5 (4H)-acetate sulfate (1:1) and is a prodrug. Clopidogrel is available as a 75 mg or 300 mg tablet.

Clopidogrel is an antiplatelet agent used to inhibit blood clots in coronary artery disease, peripheral vascular disease and cerebrovascular disease. Specifically, clopidogrel is indicated for acute coronary syndrome ("ACS"): (1) for patients with non-ST-segment elevation ACS; (2) for patients with ST-elevation myocardial infarction; and (3) recent myocardial infarction, recent stroke, or established peripheral arterial disease. Clopidogrel is also used, along with aspirin, for the prevention of thrombosis after placement of intracoronary stent or as an alternative antiplatelet drug for patients who are intolerant to aspirin.

Proton pump inhibitors (PPIs) are a group of drugs whose main action is a pronounced and long-lasting reduction of gastric acid production. Many PPIs are benzimidazole derivatives (specifically, substituted benzimidazole derivatives). Examples of some of the most common PPIs include:

Omeprazole (currently sold under the brand names: Losec, Prilosec, Zegerid, Lomac, Omepral, Omez);

Lansoprazole (currently sold under the brand names: Prevacid, Zoton, Inhibitol, Levant, Lupizole);

Dexlansoprazole (currently sold under the brand name: Dexilant);

Esomeprazole (currently sold under the brand names: Nexium, Esotrex); and

Pantoprazole (currently sold under the brand names: Protonix, Somac, Pantoloc, Pantozol, Zurcal, Zentro, Pan)

The PPIs in the above list are substituted benzimidazoles that suppress gastric acid secretion by specific inhibition of the $H^+/K^+$ ATPase enzyme system of the secretory surface of the gastric parietal cell.

Proton pump inhibitors are often prescribed with clopidogrel to reduce the risk of gastric bleeding or hemorrhage associated with the anti-platelet effect of clopidogrel therapy. There is significant ongoing concern regarding the clinical outcomes of patients taking clopidogrel and PPIs. Recently published studies suggested that PPIs have the potential to reduce the clopidogrel, G-protein coupled, (P2Y12) adenosine diphosphate (ADP) receptor (Gilard M, Arnaud B, Cornily J C, Le Gal G, Lacut K, Le Calvez G, et al. Influence of omeprazole on the antiplatelet action of clopidogrel associated with aspirin: the randomized, double-blind OCLA (Omeprazole Clopidogrel Aspirin) study. *J Am Coll Cardiol* 2008; 51(3):256-60; Pezalla E, Day D, Pulliadath I. Initial assessment of clinical impact of a drug interaction between clopidogrel and proton pump inhibitors. *J Am Coll Cardiol* 2008; 52(12): 1038-39; Ho P, Maddox T, Wang L, Fihn S, Jesse R, Peterson E, et al. Proton pump inhibitors may attentuate the benefits of clopidogrel among ACS patients: empirical evidence from 3,311 ACS patients. *Circulation* 2008; 118:S_1165. Abstract No. 6241; Aubert R, Epstein R, Teagarden J, Xia F, Yao J, Desta Z, et al. Proton pump inhibitors effect on clopidogrel effectiveness: the clopidogrel Medco outcomes study. *Circulation* 2008; 118: S_815. Abstract 3998).

Clopidogrel itself does not possess antiplatelet aggregation activity, but requires metabolism by hepatic cytochrome P450s, including CYP2C19, to an active metabolite that then blocks platelet P2Y12 receptors. Because PPIs are known inhibitors of CYP2C19, a plausible explanation for this reduced effectiveness of clopidogrel may be a metabolism-based drug-drug interaction (DDI) whereby the PPI inhibits the conversion of clopidogrel to its active metabolite by inhibiting CYP2C19. The FDA has made warnings about clinically relevant DDI with respect to clopidogrel and certain PPIs. For example, on Nov. 17, 2009, the FDA posted the following warning about a drug interaction between clopidogrel and omeprazole:

"FDA notified healthcare professionals of new safety information concerning an interaction between clopidogrel (Plavix), an anti-clotting medication, and omeprazole (Prilosec/Prilosec OTC), a proton pump inhibitor (PPI) used to reduce stomach acid. New data show that when clopidogrel and omeprazole are taken together, the effectiveness of clopidogrel is reduced. Patients at risk for heart attacks or strokes who use clopidogrel to prevent blood clots will not get the full effect of this medicine if they are also taking omeprazole. Separating the dose of clopidogrel and omeprazole in time will not reduce this drug interaction.

Other drugs that are expected to have a similar effect and should be avoided in combination with clopidogrel include: cimetidine, fluconazole, ketoconazole, voriconazole, etravirine, felbamate, fluoxetine, fluvoxamine, and ticlopidine."

Angiolillo et al. in *Clin. Pharmacology & Therapeutics*, pages 1-10 (Sep. 15, 2010), report the results of a series of four metabolic DDI studies using omeprazole, pantoprazole and clopidogrel conducted in healthy subjects. Specifically, study 1 administered a 300-mg loading dose and 75 mg/day maintenance dose of clopidogrel and omeprazole (80 mg) simultaneously to the healthy patients. Study 2 administered the clopidogrel and omeprazole of study 1 twelve (12) hours apart to the healthy patients. In study 3, the amount of clopidogrel from study 1 was increased to 600-mg loading/150 mg/day maintenance dose. Study 4 administered a 300-mg loading dose and 75 mg/day maintenance dose of clopidogrel and pantoprazole (80 mg) simultaneously to the healthy patients. The results showed that a metabolic DDI was found to exist between clopidogrel and omeprazole but not between clopidogrel and pantoprazole.

However, since not all PPIs inhibit CYP2C19 to the same extent, the potential for a clinically relevant DDI with clopidogrel may not be generalized to all PPIs. Thus, there is a need in the art for new methods of treating patients suffering from heartburn who are concomitantly being administered clopidogrel to treat a second disease state or to prevent of gastric bleeding or hemorrhage in patients being treated with clopidogrel.

SUMMARY OF THE PRESENT INVENTION

In one aspect, the present invention relates to a method of treating heartburn and at least one second disease state in a patient in need of treatment thereof. The method comprises the step of preferentially treating the patient with a therapeutically effective amount of lansoprazole, dexlansoprazole or combinations thereof to treat the heartburn, wherein the therapeutically effective amount of lansoprazole, dexlansoprazole or combinations thereof does not diminish the effectiveness of the clopidogrel bisulfate that is being concomitantly administered to treat the at least one second disease state.

In the above method, the heartburn can be associated with symptomatic non-erosive gastroesophageal reflux disease (GERD). Moreover, in the above method, the at least one second disease state is acute coronary syndrome, peripheral artery disease, myocardial infarction, stroke and combinations thereof. In the above method, the patient is preferentially treated with a therapeutically effective amount of lansoprazole. Alternatively, in the above method, the patient is preferentially treated with a therapeutically effective amount of dexlansoprazole. In still another alternative, in the above method, the patient is preferentially treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In another aspect, the present invention relates to a method of treating (such as by healing) erosive esophagitis and at least one second disease state in a patient in need thereof. This method comprises the step of preferentially treating the patient with a therapeutically effective amount of lansoprazole, dexlansoprazole or combinations thereof to treat the erosive esophagitis wherein the therapeutically effective amount of lansoprazole, dexlansoprazole or combinations thereof does not diminish the effectiveness of the clopidogrel bisulfate that is being concomitantly administered to treat the at least one second disease state.

In the above method, the at least one second disease state is acute coronary syndrome, peripheral artery disease, myocardial infarction, stroke and combinations thereof. In the above method, the patient is preferentially treated with a therapeutically effective amount of lansoprazole. Alternatively, in the above method, the patient is preferentially treated with a therapeutically effective amount of dexlansoprazole. In still another alternative, in the above method, the patient is preferentially treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In yet another aspect, the present invention relates to a method of preventing gastric bleeding or hemorrhage associated with clopidogrel therapy. This method comprises the step of administering to a patient who is concomitantly being administered or about to be administered clopidogrel bisulfate, a therapeutically effective amount of lansoprazole, dexlansoprazole or combinations thereof, wherein the therapeutically effective amount of lansoprazole, dexlansoprazole or combinations thereof does not diminish the effectiveness of the clopidogrel bisulfate that is being concomitantly administered to said patient.

In this method, the clopidogrel bisulfate is being administered to the patient to treat acute coronary syndrome, peripheral artery disease, myocardial infarction, stroke and combinations thereof. In the above method, the patient is administered a therapeutically effective amount of lansoprazole. Alternatively, in the above method, the patient is administered a therapeutically effective amount of dexlansoprazole. In still another alternative, in the above method, the patient is administered a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet another aspect, the present invention relates to a method of treating heartburn and at least one second disease state in a patient in need of treatment thereof. In this aspect, the method comprises the steps of:

a) identifying a patient suffering from heartburn and at least one second disease state, wherein said patient is being treated with or about to be treated with clopidogrel bisulfate to treat the at least one second disease state;

b) selecting from a class of proton pump inhibitors comprising omeprazole, esomeprazole, lansoprazole, dexlansoprazole or combinations thereof, at least one proton pump inhibitor to administer to the patient, wherein administration of the proton pump inhibitor to the patient does not diminish the effectiveness of the clopidogrel bisulfate that is or will be concomitantly administered to treat the at least one second disease state, wherein the proton pump inhibitor selected is dexlansoprazole, lansoprazole, or combinations thereof; and c) administering to said patient a therapeutically effective amount of dexlansoprazole, lansoprazole or combinations thereof to treat the heartburn.

In the above method, the heartburn can be associated with symptomatic non-erosive gastroesophageal reflux disease (GERD). Also, in the above method, the at least one second disease state is acute coronary syndrome, peripheral artery disease, myocardial infarction, stroke and combinations thereof. In the above method, the patient is administered a therapeutically effective amount of lansoprazole. Alternatively, in the above method, the patient is administered a therapeutically effective amount of dexlansoprazole. In still another alternative, in the above method, the patient is administered a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet another aspect, the present invention relates to a method of treating erosive esophagitis and at least one second disease state in a patient in need of treatment thereof. This method comprises the steps of:
  a) identifying a patient being treated for erosive esophagitis and at least one second disease state, wherein said patient is being treated with or about to be treated with clopidogrel bisulfate to treat the at least one second disease state,
  b) selecting from a class of proton pump inhibitors comprising omeprazole, esomeprazole, lansoprazole, dexlansoprazole or combinations thereof at least one proton pump inhibitor to administer to the patient, wherein the administration of the proton pump inhibitor to the patient does not diminish the effectiveness of the clopidogrel bisulfate that is or will be concomitantly administered to treat the at least one second disease state, wherein the proton pump inhibitor selected is dexlansoprazole, lansoprazole, or combinations thereof; and
  c) administering to said patient a therapeutically effective amount of dexlansoprazole, lansoprazole or combinations thereof to treat the erosive esophagitis.

In the above method, the patient is administered a therapeutically effective amount of lansoprazole. Alternatively, in the above method, the patient is administered a therapeutically effective amount of dexlansoprazole. In still another alternative, in the above method, the patient is administered a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet another aspect, the present invention relates to pharmaceutical compositions comprising a proton pump inhibitor and clopidogrel bisulfate, wherein the proton pump inhibitor is selected from the group consisting of: lansoprazole, dexlansoprazole and combinations thereof. The pharmaceutical compositions of the present invention can be used for the treatment of at least one of the following diseases: heartburn, erosive esophagitis, acute coronary syndrome, peripheral artery disease, myocardial infarction, stroke and combinations thereof. In the pharmaceutical compositions of the present invention, the proton pump inhibitor and clopidogrel bisulfate are administered as a single dosage form. Alternatively, in the pharmaceutical compositions of the present invention, the proton pump inhibitor and clopidogrel bisulfate are administered independently as separate dosage forms.

In still yet a further aspect, the present invention relates to a method of reducing the risk of an adverse drug interaction in a patient receiving clopidogrel bisulfate. The method comprises the step of:
  treating a patient who is concomitantly being administered a therapeutically effective amount of clopidogrel bisulfate with a therapeutically effective amount of lansoprazole, dexlansoprazole or combinations thereof to treat heartburn, wherein the therapeutically effective amount of lansoprazole, dexlansoprazole or combinations thereof does not diminish the effectiveness of the clopidogrel bisulfate and further wherein said treatment reduces a risk of an adverse drug interaction between the clopidogrel bisulfate and the lansoprazole, dexlansoprazole or combinations thereof.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet a further aspect, the present invention relates to a method of treating heartburn in a patient receiving clopidogrel bisulfate. The method comprises the step of:
  treating a patient who is concomitantly being administered a therapeutically effective amount of clopidogrel bisulfate with a therapeutically effective amount of lansoprazole, dexlansoprazole or combinations thereof to treat a heartburn, wherein the therapeutically effective amount of lansoprazole, dexlansoprazole or combinations thereof does not diminish the effectiveness of the clopidogrel bisulfate and further wherein said treatment minimizes CYP2C19 interactions between the clopidogrel bisulfate and the lansoprazole, dexlansoprazole or combinations thereof. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet a further aspect, the present invention relates to a method of selecting a heartburn treatment for use in conjunction with concomitant administration of clopidogrel bisulfate to a patient in need of treatment thereof. The method comprises the steps of:
  identifying a heartburn treatment that minimizes CYP2C19 interactions between the heartburn treatment and concomitant administration of clopidogrel bisulfate to a patient in need of treatment thereof, wherein said heartburn treatment comprises a therapeutically effective amount of lansoprazole, dexlansoprazole or combinations thereof to treat the heartburn; and selecting the heartburn treatment for use in conjunction with concomitant administration of clopidogrel bisulfate to the patient.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet another aspect, the present invention relates to a method of treating heartburn in a patient who is also concomitantly receiving clopidogrel bisulfate. The method comprises the steps of:

identifying a heartburn treatment that minimizes CYP2C19 interactions in a patient receiving concomitantly the heartburn treatment and clopidogrel bisulfate;

selecting the heartburn treatment that minimizes CYP2C19 interactions between the heartburn treatment and clopidogrel bisulfate in a patient who is to be concomitantly treated with the heartburn treatment and clopidogrel bisulfate, wherein the heartburn treatment comprises lansoprazole, dexlansoprazole or combinations thereof; and treating a patient being concomitantly administered clopidogrel bisulfate with a therapeutically effective amount of lansoprazole, dexlansoprazole or combinations thereof to treat the heartburn, wherein said lansoprazole, dexlansoprazole or combinations thereof minimize CYP2C19 interactions with the clopidogrel bisulfate.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet another aspect, the present invention relates to a method of reducing undesirable CYP2C19 interactions between a heartburn treatment and concomitant administration of clopidogrel bisulfate in a patient in need of treatment thereof. The method comprises the step of:

administering a heartburn treatment to a patient in need of treatment thereof, wherein the patient is concomitantly receiving clopidogrel bisulfate for treatment of at least one second disease state, wherein the heartburn treatment comprises a therapeutically effective amount of lansoprazole, dexlansoprazole or combinations thereof to treat the heartburn, and further wherein the therapeutically effective amount of lansoprazole, dexlansoprazole or combinations thereof does not diminish the effectiveness of the clopidogrel that is being concomitantly administered to treat the at least one second disease state and reduces undesirable CYP2C19 interactions between the lansoprazole, dexlansoprazole or combinations thereof and clopidogrel bisulfate.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In the above method, the at least one second disease state is acute coronary syndrome, peripheral artery disease, myocardial infarction, stroke and combinations thereof.

In still yet another aspect, the present invention relates to a method of treating heartburn in a patient concomitantly receiving clopidogrel bisulfate without causing significant CYP2C19 interactions between the heartburn treatment and clopidogrel bisulfate in the patient. The method comprises the step of:

administering a therapeutically effective amount of lansoprazole, dexlansoprazole or combinations thereof to a patient who is concomitantly receiving clopidogrel bisulfate to treat heartburn, wherein the therapeutically effective amount of lansoprazole, dexlansoprazole or combinations thereof does not diminish the effectiveness of the clopidogrel bisulfate and further wherein the lansoprazole, dexlansoprazole or combinations thereof do not cause significant CYP2C19 interactions with the clopidogrel bisulfate.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

In still yet another aspect, the present invention relates to a method of using lansoprazole, dexlansoprazole or combinations thereof in a patient in need of treatment thereof. The method comprises the steps of providing a patient that is concomitantly receiving clopidogrel bisulfate with a therapeutically effective amount of a heartburn treatment, wherein the heartburn treatment comprises a therapeutically effective amount of lansoprazole, dexlansoprazole or combinations thereof to treat the heartburn; and informing the patient or a medical care worker that the lansoprazole, dexlansoprazole or combinations thereof may reduce CYP2C19 interactions between the lansoprazole, dexlansoprazole or combinations and clopidogrel bisulfate.

In the above method, the heartburn may be associated with symptomatic non-erosive gastroesophageal reflux disease (GERD) or erosive esophagitis. In the above method, the patient can be treated with a therapeutically effective amount of lansoprazole. Alternatively, in the above method, the patient can be treated with a therapeutically effective amount of dexlansoprazole. Still further alternatively, in the above method, the patient can be treated with a therapeutically effective amount of a combination of lansoprazole and dexlansoprazole. In this method, the therapeutically effective amount of lansoprazole can be between about 15 mg and about 30 mg. In this method, the therapeutically effective amount of dexlansoprazole can be between about 30 mg and about 60 mg. Furthermore, in this method, the therapeutically effective amount of lansoprazole and dexlansoprazole can be between about 45 to about 90 mg.

DETAILED DESCRIPTION OF THE INVENTION

I. Definitions

Section headings as used in this section and the entire invention herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such dosages are thus encompassed by the scope of the claims reciting the terms "about" and "approximately."

As used herein, the term "active agent" refers to a proton pump inhibitor, a clopidogrel metabolite (clopidogrel is a prodrug) or combinations thereof.

The terms "administer", "administering", "administered" or "administration" refer to any manner of providing an active agent or drug (such as, a PPI or a pharmaceutically acceptable salt thereof, clopidogrel, etc.) to a subject or patient. Routes of administration can be accomplished through any means known by those skilled in the art. Such means include, but are not limited to, oral, buccal, intravenous, subcutaneous, intramuscular, transdermal, by inhalation and the like.

As used herein the term "clopidogrel" or the phrase "clopidogrel therapy" as used interchangeably herein, refers to clopidogrel bisulfate, which is sold under the brand name Plavix. The chemical name for clopidogrel is methyl (+)-(S)-α-(2-chlorophenyl)-6,7-dihydrothieno[3,2-c]pyridine-5(4H)-acetate sulfate (1:1). Clopidogrel is currently available as a 75 mg or 300 mg tablet. Clopidogrel is typically used to treat patients suffering from acute coronary syndrome, peripheral artery disease, myocardial infarction and combinations thereof.

As will be described in more detail herein, the methods of the current invention allow for clopidogrel to continue to be administered according to the manufacturer's suggested dosing of the compound. As used herein, the term "manufacturer's suggested dosing" signifies the dosing disclosed in the package insert of the clopidogrel dosage form and available in a variety of pharmaceutical treatment references. The methods of the current invention encompass the recommended dosing for all dosage forms, and include the treatment of all patients, for all disease states in which clopidogrel treatment may be effective.

The term "dosage form" refers to any solid object, semi-solid, or liquid composition designed to contain a specific pre-determined amount (i.e., dose) of a certain active agent. Suitable dosage forms may be pharmaceutical drug delivery systems, including those for oral administration, buccal administration, rectal administration, topical or mucosal delivery or subcutaneous implants, or other implanted drug delivery systems and the like. Preferably, the dosage forms described herein may be considered to be solid, however, they may contain liquid or semi-solid components. More preferably, the dosage form is an orally administered system for delivering an active agent to the gastrointestinal tract of a subject. The dosage form of the present invention may exhibit modified release of the active agent.

By an "effective amount" or a "therapeutically effective amount" of an active agent is meant a nontoxic but sufficient amount of the active agent to provide the desired effect. The amount of active agent that is "effective" will vary from subject to subject, depending on the age and general condition of the individual, the particular active agent or agents, and the like. Thus, it is not always possible to specify an exact "effective amount." However, an appropriate "effective amount" in any individual case may be determined by one of ordinary skill in the art using routine experimentation.

By "pharmaceutically acceptable," such as in the recitation of a "pharmaceutically acceptable excipient," or a "pharmaceutically acceptable additive," is meant a material that is not biologically or otherwise undesirable, i.e., the material may be incorporated into a pharmaceutical composition administered to a patient without causing any undesirable biological effects.

The phrase "proton pump inhibitor" or "PPI" refers to a compound comprising a substituted benzimidazole that suppress gastric acid secretion by specific inhibition of the $H^+/K^+$ ATPase enzyme system of the secretory surface of the gastric parietal cell. Examples of PPIs include, lansoprazole, dexlansoprazole, omeprazole, esomeprazole, pantoprazole and salts thereof. Lansoprazole is described in U.S. Pat. No. 4,628,098, omeprazole is described in U.S. Pat. No. 4,255,431, esomeprazole is described in WO 92/08716 and pantoprazole is described in U.S. Pat. No. 4,758,579. More specifically, lansoprazole is approved for the treatment of gastric acid-related diseases, specifically gastric ulcers, duodenal ulcers, reflux esophagitis, and Zollinger-Ellison syndrome (ZES). Lansoprazole is supplied in delayed-release capsules for oral administration. The delayed-release capsules contain the active ingredient in the form of enteric-coated granules and are available in 2 dosage strengths, 15 mg and 30 mg. Dexlansoprazole (the R-enantiomer of lansoprazole) delayed release capsule, also known as TAK-390MR and dexlansoprazole MR, (hereinafter referred to as dexlansoprazole capsules) was approved for the indications of healing all grades of erosive esophagitis (EE), maintenance of healed EE and treatment of heartburn associated with non-erosive gastroesophageal reflux disease. Dexlansoprazole capsules are supplied in 2 dosage strengths, 30 and 60 mg, and each consists of 2 types of granules contained within a single capsule. Each type of granule has a different pH-dependent release profile. The formulation has been designed to have approximately 25% of the drug released within 1 to 2 hours of administration, followed by a second release phase within 4 to 5 hours for the remaining 75% of the dose. Omeprazole is currently supplied in delayed-release capsules containing 10 mg, 20 mg or 40 mg in the form of enteric-coated granules. Omeprazole has been approved for the indications of short-term treatment of active duodenal ulcer, *Helicobacter pylori* eradication to reduce the risk of duodenal ulcer recurrence, gastroesophageal reflux disease (GERD), and maintenance of healing of EE. Esomeprazole is the S-isomer of omeprazole, a mixture of the S- and R-isomers. Esomeprazole is supplied in delayed-release capsules and in packets for a delayed-release oral suspension. Each delayed-release capsule contains 20 mg or 40 mg of esomeprazole in the form of enteric-coated granules. Esomeprazole has been approved for the indications of GERD, risk reduction of nonsteroidal anti-inflammatory drug (NSAID)-associated gastric ulcer, *Helicobacter pylori* eradication to reduce the risk of duodenal ulcer recurrence, and ZES. Pantoprazole is supplied as a delayed-release oral suspension, available in one strength (40 mg), and as a delayed-release tablet, currently available in two strengths (20 mg and 40 mg). Pantoprazole is indicated in adults and pediatric patients five years of age and older for the short-term treatment (up to 8 weeks) in the healing and symptomatic relief of erosive esophagitis. Pantoprazole is indicated for maintenance of healing of erosive esophagitis and reduction in relapse rates of daytime and nighttime heartburn symptoms in adult patients with GERD. Also, pantoprazole is indicated for the long-term treatment of pathological hypersecretory conditions, including ZES. Either crystalline forms or amorphous forms of the PPI can be used.

The term "subject" refers to an animal, preferably a mammal, including a human or non-human. The terms patient and subject may be used interchangeably herein.

The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease. The phrase "preferentially treating a patient" or "preferentially treating the patient" as used herein refers to the reduction in severity and/or frequency of symptoms, elimination of symptoms and/or underlying cause, prevention of the occurrence of symptoms and/or their underlying cause, and improvement or remediation of damage that is achieved by administering to the patient or subject one or more specific active agents or drugs of a certain class over one or more active agents or drugs that are members of the same class. For example, in the context of the present invention, a subject or patient who is concomitantly being administered or about to be administered clopidogrel is preferentially treated with or administered the PPIs lansoprazole, dexlansoprazole or combinations thereof instead of using one or more of other PPIs such as omeprazole, esomeprazole, pantoprazole, etc. Lansoprazole, dexlansoprazole, omeprazole, esomeprazole and pantoprazole are all PPIs; however, in the context of the present invention, patients or subjects are preferably administered lansoprazole, dexlansoprazole or combinations thereof in lieu of omeprazole, esomeprazole, pantoprazole, etc. and any combinations of omeprazole, esomeprazole, pantoprazole, etc.

II. The Present Invention

The present invention is based on the discovery that dexlansoprazole, lansoprazole and combinations thereof were found to be weak inhibitors of CYP2C19. This finding led to the further discovery that dexlansoprazole, lansoprazole and combinations thereof can be administered concomitantly with clopidogrel to a subject in need of treatment thereof without causing (1) a statistically significant change in the pharmacokinetics (AUC) in the active metabolite of clopidogrel; and (2) a statistically significant reduction in the inhibition of platelet aggregation (as a result of clopidogrel administration). Furthermore, subjects administered dexlansoprazole, lansoprazole and combinations thereof concomitantly with clopidogrel are likely to exhibit a minimal or reduced risk of experiencing any adverse drug interaction between the clopiodgrel and the lansoprazole, dexlansoprazole or combinations thereof (thus reducing the likelihood or risk to the patient that the treatment with lansoprazole, dexlansoprazole or combinations thereof would have to be stopped or discontinued). Moreover, because dexlansoprazole, lansoprazole and combinations thereof were found to be weak inhibitors of CYP2C19, subjects administered dexlansoprazole, lansoprazole and combinations thereof concomitantly with clopidogrel will experience minimized or reduced interactions between CYP2C19 and the dexlansoprazole, lansoprazole and combinations thereof and the clopidogrel. Again, such minimized or reduced interactions between CYP2C19 and the dexlansoprazole, lansoprazole and combinations thereof and the clopidogrel reduce the likelihood or risk to the patient that treatment with lansoprazole, dexlansoprazole or combinations thereof would have to be stopped or discontinued.

More specifically, the inventors of the present invention found that when dexlansoprazole and lansoprazole were administered to subjects concomitantly receiving clopidogrel therapy, that the dexlansoprazole or lansoprazole did not exhibit a significant effect on (1) the pharmacokinetics of the active metabolite of clopidogrel; and (2) the inhibition of platelet aggregation, particularly when compared to the PPI's omeprazole and esomeprazole.

Thus, in one aspect, the present invention relates to a method of treating heartburn in a patient in need of treatment thereof. The heartburn to be treated in this aspect of the present invention can be associated with symptomatic non-erosive gastroesophageal reflux disease (GERD), erosive esophagitis or combinations thereof. In this aspect, the patient in need of treatment thereof is suffering from at least one second disease state for which the patient is concomitantly being treated with clopidogrel or about to be treated with clopidogrel (namely, treatment has not yet commenced). For example, said second disease state can be acute coronary syndrome, peripheral artery disease, myocardial infarction, stroke and combinations thereof. In addition, the patient may also be suffering from a third or more disease states. An example of a third or more disease states may be any one or more of hypertension, renal disease, cancer (such as colon cancer, breast cancer, prostate cancer, bladder cancer, liver cancer, pancreatic cancer, etc), diabetes, gout, dementia, Alzheimer's Disease, arthritis, etc.

In another aspect, the present invention relates to a method of treating (e.g. healing) erosive esophagitis in a patient. In this aspect, the healing of the erosive esophagitis also includes or encompasses commencing the initial healing of erosive esophagitis as well as maintaining any level of healing of erosive esophagitis that has previously been obtained or commenced in said patient for a certain preexisting period of time (such as for one day, two days, three days, five days, one week, two weeks, three weeks, four weeks, two months, three months, four months, five months, six months, seven months, eight months, nine months, ten months, eleven months, twelve months, etc.). Also in this aspect, the patient in need of treatment thereof is suffering from at least one second disease state for which the patient is concomitantly being treated with clopidogrel or about to be treated with clopidogrel (namely, treatment has not yet commenced). For example, said second disease state can be acute coronary syndrome, peripheral artery disease, myocardial infarction, stroke and combinations thereof. In addition, the patient may also be suffering from a third or more disease states. An example of a third or more disease states may be any one or more of hypertension, renal disease, cancer (such as colon cancer, breast cancer, prostate cancer, bladder cancer, liver cancer, pancreatic cancer, etc), diabetes, gout, dementia, Alzheimer's Disease, arthritis, etc.

In another aspect, the present invention relates to methods of preventing (such as by reducing the risk) gastric bleeding or hemorrhage in a patient receiving clopidogrel therapy. This method involves administering (namely, preferentially treating) to a patient who is concomitantly being administered or about to be administered clopidogrel, a therapeutically effective amount of lansoprazole, dexlansoprazole or combinations thereof, wherein the therapeutically effective amount of lansoprazole, dexlansoprazole or combinations thereof does not diminish the effectiveness of the clopidogrel bisulfate (namely, the administration of the lansoprazole, dexlansoprazole or combinations thereof does not cause (1) a statistically significant change in the pharmacokinetics in the active metabolite of clopidogrel; and (2) a statistically significant reduction in the inhibition of platelet aggregation) that is being concomitantly administered to said patient. In this aspect of the present invention, the clopidogrel is being administered to the patient in order to treat acute coronary syndrome, peripheral artery disease, myocardial infarction, stroke and any combinations thereof.

In still yet another aspect, the present invention relates to a method of treating heartburn and at least one second disease state in a patient in need of treatment thereof. The heartburn to be treated can be heartburn associated with symptomatic non-erosive gastroesophageal reflux disease (GERD), erosive esophagitis or combinations thereof. In this aspect, the method involves first identifying a patient suffering from heartburn and at least one second disease state, wherein said patient is being treated with or about to be treated with clopidogrel bisulfate to treat the at least one second disease state. After such a patient is identified, the next step of the method involves selecting from a class of proton pump inhibitors comprising at least the PPIs omeprazole, esomeprazole, lansoprazole, dexlansoprazole or combinations thereof (the class can include other PPIs known in the art or later developed), at least one proton pump inhibitor to administer to the patient, wherein administration of the proton pump inhibitor to the patient does not diminish the effectiveness of the clopidogrel bisulfate (namely, the administration of the lansoprazole, dexlansoprazole or combinations thereof does not cause (1) a statistically significant change in the pharmacokinetics in the active metabolite of clopidogrel; and (2) a statistically significant reduction in the inhibition of platelet aggregation) that is or will be concomitantly administered to treat the at least one second disease state. Specifically, in this method, the proton pump inhibitor selected to be administered to the patient is dexlansoprazole, lansoprazole, or combinations thereof. The final step of the method involves administering to said patient a therapeutically effective amount of dexlansoprazole, lansoprazole or combinations thereof to treat the heartburn. In this aspect of the method, the second disease state can be acute coronary syndrome, peripheral artery disease, myocardial infarction, stroke and combinations thereof. In addition, the patient may also be suffering from a third or more disease states. An example of a third or more disease states may be any one or more of hypertension, renal disease, cancer (such as colon cancer, breast cancer, prostate cancer, bladder cancer, liver cancer, pancreatic cancer, etc), diabetes, gout, dementia, Alzheimer's Disease, arthritis, etc.

In still yet another aspect, the present invention relates to a method of treating (e.g. healing) erosive esophagitis and at least one second disease state, wherein said patient is being treated with or about to be treated with clopidogrel bisulfate to treat the at least one second disease state. After such a patient is identified, the next step of the method involves selecting from a class of proton pump inhibitors comprising at least the PPIs omeprazole, esomeprazole, lansoprazole, dexlansoprazole or combinations thereof (the class can include other PPIs known in the art or later developed), at least one proton pump inhibitor to administer to the patient, wherein administration of the proton pump inhibitor to the patient does not diminish the effectiveness of the clopidogrel bisulfate (namely, the administration of the lansoprazole, dexlansoprazole or combinations thereof does not cause (1) a statistically significant change in the pharmacokinetics in the active metabolite of clopidogrel; and (2) a statistically significant reduction in the inhibition of platelet aggregation) that is or will be concomitantly administered to treat the at least one second disease state. Specifically, in this method, the proton pump inhibitor selected to be administered to the patient is dexlansoprazole, lansoprazole, or combinations thereof. The final step of the method involves administering to said patient a therapeutically effective amount of dexlansoprazole, lansoprazole or combinations thereof to treat the erosive esophagitis. In this aspect of the method, the second disease state can be acute coronary syndrome, peripheral artery disease, myocardial infarction, stroke and combinations thereof. In addition, the patient may also be suffering from a third or more disease states. An example of a third or more disease states may be any one or more of hypertension, renal disease, cancer (such as colon cancer, breast cancer, prostate cancer, bladder cancer, liver cancer, pancreatic cancer, etc), diabetes, gout, dementia, Alzheimer's Disease, arthritis, etc.

In still yet another aspect, the present invention relates to a method of reducing the risk of an adverse drug interaction in a patient receiving or about to receive treatment with clopidogrel to treat a second disease state. For example, said second disease state can be acute coronary syndrome, peripheral artery disease, myocardial infarction, stroke and combinations thereof. In addition, the patient may also be suffering from third and more disease states. An example of a third and more disease states may be any one or more of hypertension, renal disease, cancer (such as colon cancer, breast cancer, prostate cancer, bladder cancer, liver cancer, pancreatic cancer, etc), diabetes, gout, dementia, Alzheimer's Disease, arthritis, etc.

In still another aspect, the present invention relates to a method of selecting a heartburn treatment for use in conjunction with concomitant administration of clopidogrel to a patient in need of treatment thereof (such as to treat a second disease state, a third disease state, a fourth disease state, etc. For example, said second disease state can be acute coronary syndrome, peripheral artery disease, myocardial infarction, stroke and combinations thereof. In addition, the patient may also be suffering from third and more disease states. An example of a third and more disease states may be any one or more of hypertension, renal disease, cancer (such as colon cancer, breast cancer, prostate cancer, bladder cancer, liver cancer, pancreatic cancer, etc), diabetes, gout, dementia, Alzheimer's Disease, arthritis, etc.)). One step of this method involves identifying a heartburn treatment that minimizes or reduces CYP2C19 interactions between the heartburn treatment and concomitant administration of clopidogrel to a patient in need of treatment thereof. Preferably, the heartburn treatment comprises a therapeutically effective amount of lansoprazole, dexlansoprazole or combinations thereof to treat the heartburn. Another step in the method involves selecting a heartburn treatment for use in conjunction with the concomitant administration of clopidogrel to the patient. In this aspect, the patient may be receiving or be about to receive treatment with clopidogrel to treat a second disease state or subsequent disease states. After selecting such a heartburn treatment pursuant to the above method, the patient receiving or about to receive treatment with clopidogrel can be treated with a therapeutically effective amount of lansoprazole, dexlansoprazole or combinations thereof to treat the heartburn, wherein said lansoprazole, dexlansoprazole or combinations thereof minimize or reduce CYP2C19 interactions with the clopidogrel.

In still another aspect, the present invention relates to a method of using lansoprazole, dexlansoprazole or combinations thereof in a patient in need of treatment thereof. One step of the method involves providing a patient that is receiving or about to clopidogrel with a therapeutically effective amount of a heartburn treatment. Preferably, the heartburn treatment comprises a therapeutically effective amount of lansoprazole, dexlansoprazole or combinations thereof to treat the heartburn. Another step of the method involves informing the patient or a medical care worker that the lansoprazole, dexlansoprazole or combinations thereof may reduce or minimize CYP2C19 interactions between the lansoprazole, dexlansoprazole or combinations thereof and clopidogrel. This step of informing the patient or medical care worker (such as a doctor, nurse, physician's assistant, emergency medical technician, etc.) that the lansoprazole, dexlansoprazole or combinations thereof may reduce or minimize CYP2C19 interactions between the lansoprazole, dexlansoprazole or combinations thereof and clopidogrel advises or notifies the patient or medical care worker that the patient is likely to have a reduced risk of experiencing an adverse drug interaction (due to the fact that lansoprazole, dexlansoprazole and combinations thereof were found to be weak inhibitors of CYP2C19) between the concomitant administration of the lansoprazole, dexlansoprazole or combinations thereof and clopidogrel.

As discussed previously herein, in the methods of the present invention, the patient is treated or preferentially treated with a therapeutically effective amount of lansoprazole, dexlansoprazole or combinations thereof wherein the therapeutically effective amount of lansoprazole, dexlansoprazole or combinations thereof does not diminish the effectiveness of the clopidogrel (namely, the administration of the lansoprazole, dexlansoprazole or combinations thereof does not cause (1) a significant change in the pharmacokinetics in the active metabolite of clopidogrel; and (2) a significant reduction in the inhibition of platelet aggregation) that is being concomitantly administered to treat the at least one second disease state. Furthermore, a patient treated pursuant to the methods of the present invention will exhibit a reduced risk of experiencing an adverse drug interaction between the clopidogrel and the lansoprazole, dexlansoprazole or combinations thereof (the lansoprazole, dexlansoprazole or combinations thereof comprising the heartburn treatment) such that treatment of the patient with the lansoprazole, dexlansoprazole or combinations thereof would not have to be discontinued. Moreover, patients treated pursuant to the methods of the present invention will exhibit a reduction in undesirable CYP2C19 interactions between the lansoprazole, dexlansoprazole or combinations thereof and clopidogrel such that treatment of the patient with the lansoprazole, dexlansoprazole or combinations thereof would not have to be stopped or discontinued.

The methods of the current invention as described herein allow for lansoprazole and dexlansoprazole to continue to be administered according to the manufacturer's suggested dosing of the compound. As used herein, the term "manufacturer's suggested dosing" signifies the dosing disclosed in the package insert of the lansoprazole and dexlansoprazole dosage forms and available in a variety of pharmaceutical treatment references. The methods of the current invention encompass the recommended dosing for all dosage forms, and include the treatment of all patients for heartburn, in which lansoprazole or dexlansoprazole may be effective. For example, 15 mg or 30 mg lansoprazole may be administered to a patient one a day. Alternatively, 30 or 60 mg dexlansoprazole may be administered to a patient once a day.

In the methods of the present invention, the order is which the lansoprazole, dexlansoprazole (or combinations thereof) and clopidogrel are each administered is not critical. The lansoprazole or dexlansoprazole can be administered before or after the administration of the clopidogrel and can also be administered at a period in time different from when the clopidogrel is administered. Also, the lansoprazole, dexlansoprazole and clopidogrel can each be administered as separate dosage forms or together in a single dosage form.

In another aspect, the present invention relates to pharmaceutical compositions comprising a proton pump inhibitor and clopidogrel bisulfate, wherein the proton pump inhibitor is selected from the group consisting of: lansoprazole, dexlansoprazole and combinations thereof. The pharmaceutical compositions of the present invention can be respectively put to use by mixing the respective active components (namely, at least one proton pump inhibitor selected from lansoprazole, dexlansoprazole or combinations thereof and clopidogrel bisulfate) either all together or independently with a physiologically acceptable carrier, excipient, binder, diluent, etc. and administering the mixture or mixtures either orally or non-orally as a pharmaceutical composition. When the active components are formulated independently, the respective formulations can be extemporaneously admixed using a diluent or the like and administered or can be administered independently of each other, either concurrently or at staggered times to the same subject.

The dosage form for said pharmaceutical composition includes such oral dosage forms as granules, powders, tablets, capsules, syrups, emulsions, suspensions, etc. and such non-oral dosage forms as injections (e.g. subcutaneous, intravenous, intramuscular and intraperitoneal injections), drip infusions, external application forms (e.g. nasal spray preparations, transdermal preparations, ointments, etc.), and suppositories (e.g. rectal and vaginal suppositories).

These dosage forms can be manufactured by the per se known technique conventionally used in pharmaceutical procedures. For example, to manufacture an oral dosage form, an excipient (e.g. lactose, sucrose, starch, mannitol, etc.), a disintegrator (e.g. calcium carbonate, carboxymethylcellulose calcium, etc.), a binder (e.g. α-starch, gum arabic, carboxymethylcellulose, polyvinylpyrrolidone, hydroxypropylcellulose, etc.), and a lubricant (e.g. talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and Eudragit™ (Rohm & Haas, Germany, methacrylic-acrylic copolymer).

Injections can be manufactured as follows. The active component or components are dissolved, suspended or emulsified in an aqueous vehicle (e.g. distilled water, physiological saline, Ringer's solution, etc.) or an oily vehicle (e.g. vegetable oil such as olive oil, sesame oil, cottonseed oil, corn oil, etc. or propylene glycol) together with a dispersant (e.g. Tween 80 (Atlas Powder, U.S.A.), HCO 60 (Nikko Chemicals), polyethylene glycol, carboxymethylcellulose, sodium alginate, etc.), a preservative (e.g. methyl p-hydroxybenzoate, propyl p-hydroxybenzoate, benzyl alcohol, chlorobutanol, phenol, etc.), an isotonizing agent (e.g. sodium chloride, glycerol, sorbitol, glucose, inverted sugar, etc.) and other additives. If desired, a solubilizer (e.g. sodium salicylate, sodium acetate, etc.), a stabilizer (e.g. human serum albumin), a soothing agent (e.g. benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g. lactose, mannitol, starch, microcrystalline cellulose, sucrose, etc.), a thickener (e.g. natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions—may optionally contain a pH control agent (e.g. carbonic acid, phosphoric acid, citric acid, hydrochloric acid, sodium hydroxide, etc.), and a preservative (e.g. p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides (e.g. cacao butter, Witepsols (Dynamit-Nobel), etc.), medium-chain fatty acids (e.g. Migriols (Dynamit-Nobel), etc.), vegetable oils (e.g. sesame oil, soybean oil, cotton-seed oil, etc.), etc. The water-soluble base includes, for instance, polyethylene glycols, propylene glycol, etc. The hydrophilic base includes, for instance, natural gums, cellulose derivatives, vinyl polymers, and acrylic polymers, etc.

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the lansoprazole can be 15 mg or 30 mg. The dosage of dexlansoprazole can be 30 mg and 60 mg. The dosage of clopidogrel bisulfate can be 75 mg. Such amounts can be readily determined by those skilled in the art.

By way of example, and not of limitation, an example of the present invention shall now be given.

EXAMPLE 1

A Phase 1, Randomized, Open-Label, 2-Period, Crossover Design Study to Assess the Effects of Multiple Oral Doses of Dexlansoprazole, Lansoprazole, Omeprazole or Esomeprazole on the Steady-State Pharmacokinetics and Pharmacodynamics of Clopidogrel in Healthy Subjects Objectives
Primary:
The primary objective was to assess the potential for dexlansoprazole, lansoprazole, omeprazole or esomeprazole to affect the steady-state pharmacokinetics and pharmacodynamics of clopidogrel.
Secondary:
The secondary objective was to assess the safety of multiple doses of clopidogrel in combination with dexlansoprazole, lansoprazole, omeprazole or esomeprazole in healthy subjects.
Methodology
This was a phase 1, randomized, open-label, single-center, multiple-dose, 2-period crossover study to assess the effects of multiple oral (PO) doses of dexlansoprazole, lansoprazole, omeprazole, or esomeprazole on the steady-state pharmacokinetics and pharmacodynamics of clopidogrel in healthy subjects who satisfied the selection criteria, were randomized equally into 8 regimen sequence groups, 20 subjects each, according to the following proton pump inhibitor (PPI) groups:

| PPI Group | Regimen Sequence Group | N | Period 1 | Period 2 |
|---|---|---|---|---|
| 1 | 1 | 20 | A | B |
|   | 2 | 20 | B | A |
| 2 | 3 | 20 | A | C |
|   | 4 | 20 | C | A |
| 3 | 5 | 20 | A | D |
|   | 6 | 20 | D | A |
| 4 | 7 | 20 | A | E |
|   | 8 | 20 | E | A |

Regimen A: 75 mg clopidogrel once daily (QD) for 9 Days.
Regimen B: 75 mg clopidogrel + 30 mg lansoprazole QD for 9 days.
Regimen C: 75 mg clopidogrel + 60 mg dexlansoprazole QD for 9 days.
Regimen D: 75 mg clopidogrel + 80 mg (2 x 40 mg) omeprazole QD for 9 days.
Regimen E: 75 mg clopidogrel + 40 mg esomeprazole QD for 9 days.

Number of Subjects:
Planned: 160 subjects
Safety Set: 160 subjects; Pharmacokinetic Set: 158 subjects; Pharmacodynamic Set: 158 subjects
Diagnosis and Main Criteria for Inclusion:
Healthy subjects aged 18 to 55 years old, inclusive, who had a body mass index (BMI) between 18 and 30 kg/m$^2$ inclusive, and who were capable of understanding and complying with protocol requirements. Subjects were in good health as determined by the investigator (i.e., via medical history, laboratory test results, electrocardiogram

[ECG], vitals and physical exam). Subjects signed a written, informed consent form prior to initiation of study procedures. The subject was a CYP2C19 extensive metabolizer (wt/wt).

Test Product, Dose and Mode of Administration

Plavix (clopidogrel) 75 mg tablets, administered with one of the following four PPIs:

- Dexilant (dexlansoprazole) 60 mg capsules (30 count bottle), Takeda Pharmaceuticals America, Inc./60 mg PO
- Prevacid (lansoprazole) 30 mg capsules (100 count bottle), Takeda Pharmaceuticals America, Inc./30 mg PO
- Omeprazole 80 mg capsules (2×40 mg capsules), (30 count bottle), Watson Pharmaceuticals, Inc./80 mg PO
- Nexium (esomeprazole) 40 mg capsules (30 count bottle), AstraZeneca./40 mg PO Duration of Treatment:

There were 9 days of dosing in each of the 2 periods, which were 18 days of dosing in total. There was a washout interval of 10 to 14 days between the last dose of study drug in Period 1 and the first dose of study drug in Period 2.

Clopidogrel 75 mg, QD, was given for 9 days in each of the two periods. Lansoprazole 30 mg, dexlansoprazole 60 mg, omeprazole 80 mg (2×40 mg), or esomeprazole 40 mg, QD, was given for 9 days in 1 of the 2 periods, depending on the randomization schedule.

Reference Therapy, Dose and Mode of Administration

Plavix (clopidogrel) 75 mg tablets (90 count bottle), Sanofi-Aventis/75 mg PO administered alone.

Criteria for Evaluation:

Pharmacokinetics: On Day 9 of each period, blood samples were collected at predose and for 24 hours postdose to measure plasma concentrations of clopidogrel and clopidogrel active and inactive metabolites. Pharmacokinetic parameters were derived using non-compartmental analysis methods determined from the concentration-time data for all evaluable subjects. Actual sampling times were used in all computations involving sampling times. The following PK parameters were calculated: the peak plasma concentration (Cmax), time to reach the peak concentration (Tmax), area under the plasma concentration-time curve from time 0 to the time of last quantifiable concentration (AUC(0-tlqc)), area under the plasma concentration-time curve from time 0 to tau over a dosing interval, where tau is the length of the dosing interval (AUC(0-tau)), apparent terminal elimination half life (T1/2), and the apparent terminal elimination rate constant ($\lambda z$).

Pharmacodynamics: Platelet function was assessed on Day-1, Days 7 to 9 prior to the dose of clopidogrel and 24-hours post Day 9 dose in each period. The pharmacodynamic parameters activated by clopidogrel were determined from 3 platelet function tests: Vasodilator-stimulated phosphoprotein (VASP), Aggregometry with adenosine diphosphate (ADP) and VerifyNow®. Platelet reactivity index (PRI), maximum platelet aggregation (MPA) with 5 and 20 µM ADP, and P2Y12 platelet reactivity unit (PRU) were evaluated from these 3 tests, respectively.

Safety: Safety variables included treatment-emergent adverse events (TEAEs), serious adverse events (SAEs), clinical laboratory testing (hematology, serum chemistry, and urinalysis), physical examination findings, vital sign measurements, and 12-lead (ECG) results.

Statistical Methods:

For each PPI group, on Day 9 of each period, plasma concentrations of clopidogrel, the active and inactive metabolites of clopidogrel and their pharmacokinetic parameters were tabulated and descriptive statistics computed by regimens. To assess the effect of multiple doses of the PPIs on the pharmacokinetics of clopidogrel and clopidogrel's active and inactive metabolite, analyses of variance (ANOVA) models with factors of sequence, period, regimen and subjects within sequence were used to compare these analytes: Tmax, $\lambda z$, and the natural logarithm of Cmax, AUC(0-tlqc) and AUC(0-tau) values on Day 9 in the presence and absence of a PPI. The ratio of clopidogrel with each PPI's central value to that from the clopidogrel alone was determined for Cmax and AUC(s) by exponentiating the difference between the least square means of logarithms. Additionally, for Cmax and AUC(s), 90% confidence intervals (CIs) for the ratio of regimen central values were determined by exponentiating the endpoints of 90% CIs for the difference of logarithms. A conclusion of no effect of the PPIs on the PK of clopidogrel and clopidogrel's active and inactive metabolite was reached if the 90% CIs for the ratio of regimen central values for their Cmax and AUC(s) were within the 0.80 to 1.25 interval.

For each PPI group, at 24 hrs post Day 9 dose of both periods, pharmacodynamic parameters from the platelet function tests were tabulated and descriptive statistics computed by regimens. ANOVA models with sequence, subject within sequence, period and regimen were fitted to the pharmacodynamic parameters. Pairwise comparison between regimen of clopidogrel with a PPI and clopidogrel alone was conducted within the framework of ANOVA. To assess the effect of multiple doses of 1 of the 4 PPIs on the pharmacodynamics of clopidogrel, 90% CIs for the least square mean difference between the 2 regimens for PRI were provided within the framework of ANOVA. A conclusion of no effect of each PPI on the pharmacodynamics of clopidogrel was reached if the 90% CI for the difference in the least square means of PRI was within the −15% to 15% interval.

For each PPI group, adverse events (AEs) that started or worsened in severity after the first dose of study drug were summarized by regimens. Adverse events were classified according to the Medical Dictionary for Regulatory Activities (MedDRA) system organ class (SOC) and preferred term (PT), and were tabulated with a breakdown by regimen within PPI group and by event severity. Similar AE tabulations were performed on those events assessed by the investigator as related to study drug. Baseline, postdose, and change from baseline to postdose laboratory values were summarized utilizing descriptive statistics for each regimen. A table with predefined criteria for markedly abnormal values for laboratory variables is presented. Individual subject data with markedly abnormal laboratory values are presented. Similarly, vital signs were summarized for each regimen in each PPI group by presenting descriptive statistics for baseline, postdose, and change from baseline to postdose values. A table with predefined criteria for abnormal changes from baseline for vital sign variables is presented. Individual subject data with abnormal changes from baseline for vital sign variables is presented.

Summary of Results

Subject Disposition: A total of 160 subjects (mean [SD] age of 33.9 [7.26] years), including 80 male and 80 female subjects, were randomized in the study from the 552 unique subjects who were screened. One hundred and fifty subjects completed study drug. Two subjects in PPI Group 1, 4 subjects in PPI Group 2, 2 subject in PPI Group 3 and 2 subjects in PPI Group 4 prematurely discontinued study drug. The most common reasons for premature discontinuation were major protocol violation and adverse event. Each PPI group contained an equal number of men (N=20) and women (N=20). Subjects were predominantly White (98.1%). Overall mean (SD) BMI was 26.1 (2.32) kg/m².

Pharmacokinetic Results: Following administration of clopidogrel 75 mg concomitantly with dexlansoprazole 60 mg or lansoprazole 30 mg for 9 days, mean plasma exposure (Cmax and AUCs) for clopidogrel active metabolite were slightly less when compared to those values for clopidogrel alone. The decreases in clopidogrel active metabolite plasma exposure were greater than with dexlansoprazole or lansoprazole when clopidogrel 75 mg was administered with omeprazole 80 mg or esomeprazole 40 mg for 9 days compared to clopidogrel alone. A summary of the PK parameter estimates of clopidogrel active metabolite following clopidogrel 75 mg PO alone and after multiple PO doses of dexlansoprazole 60 mg, lansoprazole 30 mg, omeprazole 80 mg, or esomeprazole 40 mg is presented below in Table 1:

TABLE 1

|  | Tmax (a) (hr) | Cmax (ng/mL) | AUC(0-tlqc) (ng hr/mL) | AUC(0-tau) (ng hr/mL) |
|---|---|---|---|---|
| Lansoprazole PPI Group 1 - Clopidogrel Active Metabolite Clopidogrel Alone | | | | |
| N | 38 | 38 | 38 | 38 |
| Mean | 0.50 | 39.14 | 41.69 | 42.07 |
| SD | 0.50/1.50 | 12.55 | 10.02 | 10.06 |
| CV % | NA | 32 | 24 | 24 |
| Clopidogrel with Lansoprazole 30 mg | | | | |
| N | 38 | 38 | 38 | 38 |
| Mean | 0.50 | 30.01 | 36.42 | 36.71 |
| SD | 0.50/4.00 | 15.26 | 10.83 | 10.72 |
| CV % | NA | 51 | 30 | 29 |
| Dexlansoprazole PPI Group 2 - Clopidogrel Active Metabolite Clopidogrel Alone | | | | |
| N | 36 | 36 | 36 | 36 |
| Mean | 0.50 | 38.85 | 41.25 | 41.52 |
| SD | 0.50/1.50 | 15.70 | 14.69 | 14.67 |
| CV % | NA | 40 | 36 | 35 |
| Clopidogrel with Dexlansoprazole 60 mg | | | | |
| N | 36 | 36 | 36 | 36 |
| Mean | 0.50 | 29.33 | 37.75 | 38.04 |
| SD | 0.50/1.50 | 12.40 | 13.13 | 12.99 |
| CV % | NA | 42 | 35 | 34 |
| Omeprazole PPI Group 3 - Clopidogrel Active Metabolite Clopidogrel Alone | | | | |
| N | 38 | 38 | 38 | 38 |
| Mean | 0.50 | 38.25 | 37.78 | 38.04 |
| SD | 0.50/1.00 | 12.46 | 12.04 | 12.08 |
| CV % | NA | 33 | 32 | 32 |
| Clopidogrel with Omeprazole 80 mg | | | | |
| N | 38 | 38 | 38 | 38 |
| Mean | 0.50 | 22.55 | 26.28 | 26.51 |
| SD | 0.50/3.00 | 10.68 | 8.80 | 8.84 |
| CV % | NA | 47 | 33 | 33 |
| Esomeprazole PPI Group 4 - Clopidogrel Active Metabolite Clopidogrel Alone | | | | |
| N | 38 | 38 | 38 | 38 |
| Mean | 0.50 | 40.98 | 42.35 | 42.62 |
| SD | 0.50/1.50 | 22.91 | 18.79 | 18.82 |
| CV % | NA | 56 | 44 | 44 |
| Clopidogrel with Esomeprazole 40 mg | | | | |
| N | 38 | 38 | 38 | 38 |
| Mean | 0.50 | 24.69 | 31.23 | 31.52 |
| SD | 0.50/1.50 | 10.64 | 9.94 | 9.89 |
| CV % | NA | 43 | 32 | 31 |

NA = not applicable.

(a) Descriptive statistics for Tmax is median, minimum and maximum.

The 90% CIs for the ratio of the central values for the clopidogrel active metabolite AUCs for clopidogrel with dexlansoprazole 60 mg or lansoprazole 30 mg compared with clopidogrel alone were within the 0.80 to 1.25 no effect boundary. Coadministration of clopidogrel with dexlansoprazole 60 mg or lansoprazole 30 mg for 9 days resulted in an approximately 30% decrease in clopidogrel active metabolite Cmax when compared with clopidogrel alone. The 90% CIs for the ratio of the central value for the clopidogrel active metabolite Cmax when clopidogrel was administered with dexlansoprazole 60 mg or lansoprazole 30 mg were outside the 0.80 to 1.25 no effect boundary when compared with clopidogrel alone. Administration of clopidogrel with omeprazole 80 mg or esomeprazole 40 mg resulted in a 16% to 44% decrease in clopidogrel active metabolite Cmax and AUCs when compared with clopidogrel alone. The 90% CI for the ratio of the central value for the clopidogrel active metabolite Cmax and AUCs when clopidogrel was administered with either omeprazole 80 mg or esomeprazole 40 mg extended below the lower no effect boundary of 0.80 when compared with clopidogrel alone. A summary of the point estimates and 90% CIs for the PPI groups are presented in the following Table 2:

TABLE 2

| Parameter | Point Estimate | 90% CI |
|---|---|---|
| Lansoprazole PPI Group 1 Clopidogrel Active Metabolite | | |
| Cmax | 0.7000 | (0.6106-0.8026) |
| AUC(0-tlqc) | 0.8573 | (0.8020-0.9165) |
| AUC(0-tau) | 0.8578 | (0.8039-0.9154) |
| Dexlansoprazole PPI Group 2 Clopidogrel Active Metabolite | | |
| Cmax | 0.7340 | (0.6516-0.8269) |
| AUC(0-tlqc) | 0.9103 | (0.8567-0.9672) |
| AUC(0-tau) | 0.9127 | (0.8597-0.9690) |
| Omeprazole PPI Group 3 Clopidogrel Active Metabolite | | |
| Cmax | 0.5564 | (0.4877-0.6347) |
| AUC(0-tlqc) | 0.6943 | (0.6438-0.7487) |
| AUC(0-tau) | 0.6955 | (06449-0.7499) |
| Esomeprazole PPI Group 4 Clopidogrel Active Metabolite | | |
| Cmax | 0.6783 | (0.5063-0.9087) |
| AUC(0-tlqc) | 0.8389 | (0.6440-1.0928) |
| AUC(0-tau) | 0.8359 | (0.6503-1.0744) |

Pharmacodynamic Results:

Following administration of clopidogrel alone for 9 days, the mean PRI was approximately 41% to 48% across the four PPI groups. Following administration of clopidogrel with lansoprazole 30 mg or dexlansoprazole 60 mg, the mean PRI increased 4.1% and 2.0% respectively, while clopidogrel with omeprazole 80 mg and esomeprazole 40 mg resulted in the mean PRI increasing by more than 11%. The results of ANOVA models applied to PRI 24 hours post Day 9 dose of clopidogrel when administered with and without a PPI in subjects with complete data for both regimens are provided in the following Table 3:

TABLE 3

| PPI Group | Difference in the LS-Means of PRI (with PPI vs without PPI) | 90% CI |
|---|---|---|
| Lansoprazole 30 mg | 4.1016 | (0.0348, 8.1684) |
| Dexlansoprazole 60 mg | 2.0474 | (−0.8555, 4.9503) |
| Omeprazole 80 mg | 11.0407 | (6.5219, 15.5595) |
| Esomeprazole 40 mg | 11.4437 | (7.1791, 15.7083) |

For the lansoprazole 30 mg and dexlansoprazole 60 mg PPI groups, the upper bounds of 90% CIs for the difference in the LS-Means were less than 15%; therefore, the equivalence in PD was demonstrated between clopidogrel alone and clopidogrel with lansoprazole 30 mg or dexlansoprazole 60 mg regimen in terms of PRI. The lower bound of the 90% CI for the omeprazole 80 mg group is much greater than 0; therefore the effect of omeprazole 80 mg on clopidogrel PD was confirmed. The effect of esomeprazole 40 mg on clopidogrel PD was very similar to omeprazole 80 mg, as the upper bound of the 90% CI extended above the 15% boundary.

Following administration of clopidogrel with dexlansoprazole 60 mg, the difference when compared with clopidogrel alone in either MPA was not statistically significant (p-value>0.05). When clopidogrel was administered with lansoprazole 30 mg, the differences when compared with clopidogrel alone in MPA were similar to dexlansoprazole 60 mg but statistically significant. For both dexlansoprazole 60 mg and lansoprazole 30 mg, the mean differences were not more than 5%. Compared with clopidogrel alone, clopidogrel with omeprazole 80 mg or with esomeprazole 40 mg increased MPA with both 5 μM and 20 μM by 8 to 10% and these effects were statistically significant. The results of the analyses of MPA at 24 hours post Day 9 dose for subjects with complete data in each PPI group are provided in the following Table 4:

TABLE 4

| PPI Group | Clopidogrel Alone Mean (SD) | Clopidogrel + PPI Mean (SD) | P-Values |
|---|---|---|---|
| MPA with 5 μM ADP (%) at 24 Hours Post Day 9 Dose | | | |
| Lansoprazole 30 mg | 28.1 (6.76) | 30.8 (9.35) | 0.035* |
| Dexlansoprazole 60 mg | 34.6 (14.23) | 36.2 (16.87) | 0.445 |
| Omeprazole 80 mg | 34.2 (12.32) | 42.5 (14.74) | <0.001*** |
| Esomeprazole 40 mg | 29.3 (10.41) | 38.2 (17.77) | <0.001*** |
| MPA with 20 μM ADP (%) at 24 Hours Post Day 9 Dose | | | |
| Lansoprazole 30 mg | 36.7 (9.11) | 41.6 (12.65) | 0.004** |
| Dexlansoprazole 60 mg | 43.1 (13.24) | 46.3 (16.93) | 0.148 |
| Omeprazole 80 mg | 43.5 (14.00) | 53.5 (13.75) | <0.001*** |
| Esomeprazole 40 mg | 39.3 (13.22) | 47.9 (15.77) | <0.001*** |

*, , *p-value < 0.05, 0.01 and 0.001, respectively.

Compared with clopidogrel alone, the increases in PRU when clopidogrel was coadministered with either dexlansoprazole 60 mg, lansoprazole 30 mg, omeprazole 80 mg, or esomeprazole 40 mg were statistically significant; however, these changes were greatest for omeprazole 80 mg and esomeprazole 40 mg (>50 units increase) compared with dexlansoprazole 60 mg and lansoprazole 30 mg (<20 units increase). The results of the analyses of the PRU at 24 hours postdose on Day 9 in subjects with complete data for both regimens are provided in the following Table 5:

TABLE 5

| PPI Group | Clopidogrel Alone Mean (SD) | Clopidogrel + PPI Mean (SD) | P-Values |
|---|---|---|---|
| PRU (%) at 24 Hours Post Day 9 Dose | | | |
| Lansoprazole 30 mg | 114.9 (56.44) | 131.8 (71.27) | <0.001*** |
| Dexlansoprazole 60 mg | 124.2 (79.10) | 146.7 (84.45) | 0.024** |
| Omeprazole 80 mg | 133.0 (67.62) | 201.5 (59.65) | <0.001*** |
| Esomeprazole 40 mg | 121.1 (50.64) | 177.6 (55.37) | <0.001*** |

*, , *p-value < 0.05, 0.01 and 0.001, respectively.

Safety Results:

Overall, 103 (64%) of 160 subject experienced 1 or more TEAEs. The number of subjects with treatment-related AEs were 81 (51%) of 160 subjects. All TEAEs were mild or moderate in severity.

In all PPI groups, regardless of regimen, the most common AEs were headaches and gastrointestinal disorders, which included nausea and abdominal pain. Events of ecchymosis, which is a characteristic of clopidogrel exposure, were reported in nearly all regimens and most were considered to be related to study drug.

One subject experienced an SAE of serum sickness-like reaction that was considered to be related to study drug. Three subjects experienced TEAEs that lead to premature discontinuation from the study. During physical examination, one subject reported neurological changes from Baseline described as generalized and symmetrical weakness in both legs and fatigue, with slow voluntary movements and rate of speech. These were considered to be AEs and the subject was prematurely discontinued. Elevated pulse rates were observed in several subjects; however, these subjects with sporadic increases in pulse rates had normal blood pressure and rates of respiration as well as ECG readings at the times when their pulse rates were higher than normal. No clinically meaningful changes from baseline or markedly abnormal values were observed for any chemistry or hematology values or ECG character values.

Conclusions

This study confirmed that the positive control, omeprazole 80 mg, significantly affected the pharmacokinetics of clopidogrel active metabolite and reduced clopidogrel's inhibition of platelet aggregation. The effect of esomeprazole 40 mg on the pharmacokinetics of clopidogrel active metabolite and inhibition of platelet aggregation was also significant to a similar degree as that of omeprazole 80 mg. In contrast, the effect of dexlansoprazole 60 mg or lansoprazole 30 mg on the pharmacokinetics of clopidogrel active metabolite and clopidogrel's inhibition of platelet aggregation was not significant and/or less than those of omeprazole 80 mg or esomeprazole 40 mg. These results suggest that the potential effects of PPIs on clopidogrel's activity could be minimized by use of dexlansoprazole or lansoprazole (weak CYP2C19 inhibitors) rather than esomeprazole or omeprazole (potent CYP2C19 inhibitors).

What is claimed is:

1. A method of treating heartburn or erosive esophagitis and at least one second disease state in a patient in need of treatment thereof, the method comprising:
   a) identifying a patient suffering from heartburn or erosive esophagitis and at least one second disease state, wherein said patient is being treated with or about to be treated with clopidogrel to treat the at least one second disease state;
   b) preferentially selecting dexlansoprazole from a group of proton pump inhibitors to administer to the patient; and
   c) concomitantly administering separate dosage forms of clopidogrel and a therapeutically effective amount of dexlansoprazole to said patient in need of treatment thereof;
wherein the therapeutically effective amount of dexlansoprazole is a dose of 30 mg.

2. The method of claim 1, wherein the heart burn is heartburn associated with symptomatic non-erosive gastroesophageal reflux disease.

3. The method of claim 1, wherein the administration of the dexlansoprazole to the patient does not inhibit CYP2C19 interactions between the dexlansoprazole and clopidogrel.

4. The method of claim 1, wherein the pharmacological activity of the clopidogrel that is administered is to concomitantly treat the at least one second disease state.

5. The method of claim 1, wherein the at least one second disease state is acute coronary syndrome, peripheral artery disease, myocardial infarction, stroke or a combinations thereof.

6. A method of treating heartburn or erosive esophagitis in a patient concomitantly receiving clopidogrel without inhibiting CYP2C19 interactions between the heartburn or esophagitis treatment and clopidogrel in the patient, the method comprising the step of:
   preferentially administering a therapeutically effective amount of dexlansoprazole to a patient who is concomitantly receiving clopidogrel to treat heartburn or erosive esophagitis, wherein the therapeutically effective amount of dexlansoprazole does not (i) inhibit the pharmacological activity of the clopidogrel; and (ii) inhibit CYP2C19 interactions between the dexlansoprazole and the clopidogrel,
   wherein the therapeutically effective amount of dexlansoprazole is a dose of 30 mg.

7. The method of claim 6, wherein the heartburn is heartburn associated with symptomatic non-erosive gastroesophageal reflux disease.

8. The method of claim 6, wherein the at least one second disease state is acute coronary syndrome, peripheral artery disease, myocardial infarction, stroke or a combinations thereof.

9. The method of claim 1, wherein the treatment of erosive esophagitis comprises healing erosive esophagitis.

10. The method of claim 6, wherein the treatment of erosive esophagitis comprises healing erosive esophagitis.

* * * * *